United States Patent [19]

Perkinson

[11] 4,153,970

[45] May 15, 1979

[54] DOOR HANDGRIP WITH FINGERPRINT RECORDING SURFACE

[76] Inventor: Benjamin J. Perkinson, 310 Spalding Dr., Beverly Hills, Calif. 90212

[21] Appl. No.: 795,200

[22] Filed: May 9, 1977

[51] Int. Cl.² ............................................. E05B 1/00
[52] U.S. Cl. .................................... 16/111 R; 49/70; 109/2; 118/31.5
[58] Field of Search ........ 16/111 R, DIG. 12, 116 R, 16/116 A, 110 R; 118/31.5; 292/DIG. 2; 109/2, 25, 44; 49/17, 70, 460

[56] References Cited

U.S. PATENT DOCUMENTS

| 155,105 | 9/1874 | Pauly | 49/17 |
| 1,389,477 | 8/1921 | Beeman | 16/DIG. 12 |
| 1,850,602 | 3/1932 | Pineo | 292/DIG. 2 |

*Primary Examiner*—John McIntosh
*Attorney, Agent, or Firm*—Sellers and Brace

[57] ABSTRACT

A door handgrip having means for obtaining a fingerprint of the next person using the door, as a bank robber or a law breaker. For this purpose the grip is provided with a pair of fingergrip surfaces one of which is in normal use and the other of which is print-free and normally shielded from use. Remote control means is operable to replace the normally used gripping surface with the print-free surface thereby to obtain the fingerprints of the next person using the grip.

12 Claims, 5 Drawing Figures

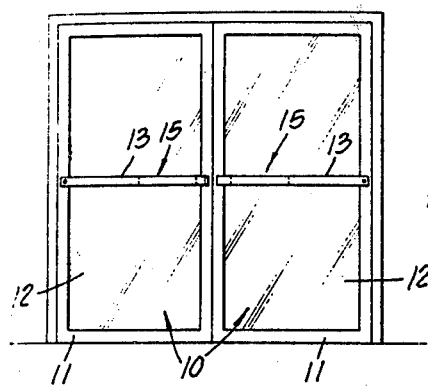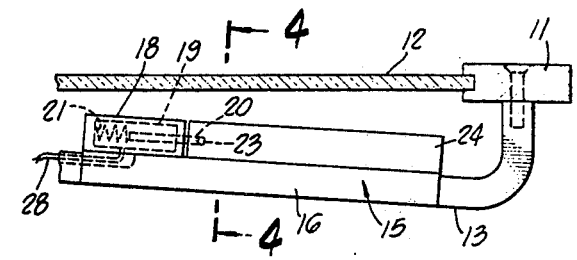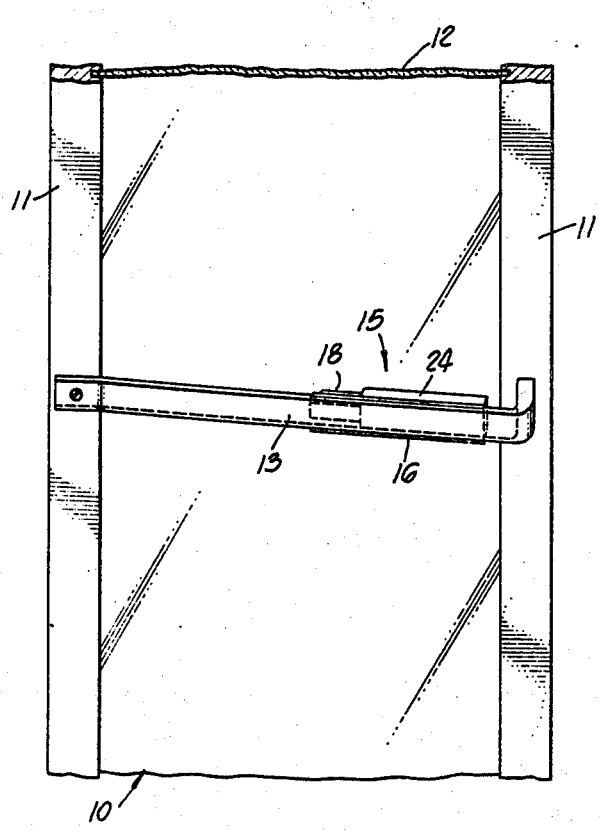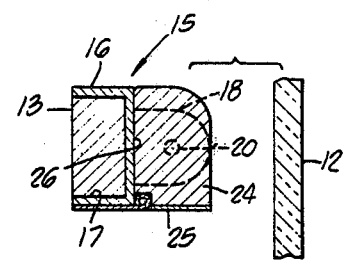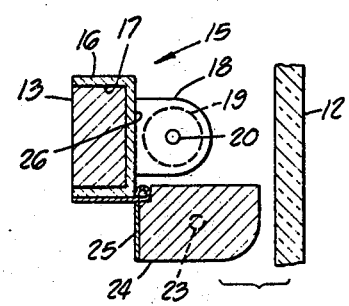
FIG. 1.
FIG. 2.
FIG. 3.
FIG. 4.
FIG. 5.

DOOR HANDGRIP WITH FINGERPRINT RECORDING SURFACE

This invention relates to door handgrips, and more particularly to an improved grip having provision for obtaining the finger prints of the next person using the door after actuation of remote control means to expose a print-free surface of the handgrip.

The door handgrip provided by this invention has general application on doors of all types and more particularly on doors of banks and the like public buildings frequently burglarized or the subject of holdups. Various proposals have been made for obtaining a record of the identity of such persons including cameras and closed circuit television monitoring systems arranged to photograph or obtain images of the law breaker on the scene but these techniques frequently provide images of little or no value for well known reasons.

The present invention provides simple, remotely controllable means for obtaining fingerprints of the criminal as an incident to his leaving the premises. This is accomplished by providing any conventional door to the premises through which the criminal must exit with specially constructed handgrips. These handgrips are provided with dual or alternate finger gripping surfaces one of which is print-free and shielded from use normally but which can be quickly exposed by any one on the premises having access to remote control means. Care is then exercised not to permit anyone else to use the hand grips until the police officials have removed or made copies of the fingerprints left by the criminal.

Accordingly, it is a primary object of this invention to provide a door handgrip with a pair of finger grip surfaces one of which is maintained print-free and shielded from use but is arranged to be quickly exposed to record the fingerprints of a criminal leaving the premises.

Another object of the invention is to provide a simple, rugged fingerprint recording accessory readily installed on a door handgrip and arranged to be armed by remote control to obtain the fingerprints of the next person to use the handgrip.

These and other more specific objects will appear upon reading the following specification and claims and upon considering in connection therewith the attached drawing to which they relate.

Referring now to the drawing in which a preferred embodiment of the invention is illustrated:

FIG. 1 is an elevational view of a pair of building doors each equipped with an illustrative embodiment of the invention handgrip;

FIG. 2 is a fragmentary perspective view on an enlarged scale of the handgrip;

FIG. 3 is a fragmentary view on an enlarged scale showing the cover of the device in its normal closed position;

FIG. 4 is a cross-sectional view taken along line 4—4 on FIG. 3; and

FIG. 5 is a cross-sectional view similar to FIG. 4 but showing the normally closed cover in open position to expose the fingerprint recording surface.

Referring initially more particularly to FIG. 1, there is shown a pair of doors 10,10 supported on suitable hinges along their outer vertical edges. As shown these doors are provided with a metal frame 11 supporting a full length glass panel 12. Each door is equipped with an L-shaped metal handgrip 13 of non-magnetic material secured to frame 11 in any suitable manner.

The invention fingerprint recording device, designated generally 15, has a channel-shaped mounting frame 16 sized to embrace hand grip 13 from the inner side thereof. This frame preferably has a snug fit over the main hand grip and may be secured thereto either by fasteners, not shown, or by a layer of strong adhesive 17. Enclosed within a casing 18 rigidly secured to frame 16 is a solenoid 19. This solenoid embraces an armature 20 spring biased by a compression spring 21 to the extended position shown in FIG. 3.

Normally, solenoid 19 is de-energized and its armature 20 is held in its extended position shown in FIG. 3. Under these conditions the armature is seated in a latching bore 23 (FIG. 5) formed in the adjacent end of a cover 24 hinged, as shown in FIGS. 4 and 5 to the lower longitudinal edge of frame 16 by hinge 25. This hinge is so constructed that it supports cover 24 in the position shown in FIG. 5 when released from its latched position by the retraction of armature 20.

Cover 24 extends along a major length of the hand grip 13 so as to conceal and protect a secondary hand grip and high-fidelity fingerprint recording surface 26 along the outer surface of frame member 16. Normally, however, cover 24 is in its closed position shown in FIG. 4 thereby safeguarding and protecting surface 26 from contact by the finger tips of persons using doors 10.

Solenoid 19 is provided with electrical lead wires 28 which are connected in circuit with a suitable power source and a series of switches connected in parallel and the closing of any one of which energizes the solenoid to retract armature 20. The cover 24 immediately pivots through an arc of 90° to its open position, it being understood that hinge 25 is preferably constructed to support the open cover in the position shown in FIG. 5. When the cover is swung to its closed upright position the latching bore 23 is in position to receive the outer end of armature 20.

From the foregoing it will be recognized that the invention fingerprint recording device is readily installed on the hand grips of the main doors of a public building, such as a bank or the like, with the fingerprint protective cover 24 preferably extending along the rear side of the surface of the hand grip normally used by persons leaving the building. The lead wires 28 for the solenoid are suitably secured along the hinged edge of the door frame from which they extend to areas of the building normally occupied by building employees. As many activating switches as desired may be connected to the solenoid.

Normally the solenoid is deactivated and spring 21 maintains the armature extended thereby latching cover 24 in its closed position to protect the clean polished fingerprint recording surface 26. Should a criminal or other wrongdoer attempt to leave the building equipped with the invention fingerprint recording device, any employee may close one of the switches to energize the solenoid, retract armature 20 and release cover 24 to its open position. The criminal will instinctively grasp the recording surface 26 as he opens the door to make his escape and unconsciously leave a clear print of each fingertip in contact with this surface. If police or security personnel are at hand, the fresh fingerprints may be lifted and photographed using well known print recording techniques. If the door is equipped with a glass plane 12, the photograph can be taken therethrough; otherwise, a mirror may be used to photograph the prints. If such personnel are not immediately available it is a simple matter to preserve the fingerprints simply by reclosing and relatching cover 24 in its closed position until such time as police personnel are available to lift the prints from the handgrip.

While the particular door handgrip with fingerprint recording surface herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. That improvement in a handgrip for a building door constructed to obtain the fingerprints of a criminal comprising a handgrip having a main body, said main body having means providing first and second surfaces adapted to be contacted by the fingertips of persons using said handgrip each usable to open a door equipped with said handgrip and so arranged that only said first surface is normally exposed for contact with the fingertips, and means operable from a remote control station for quickly replacing said first surface with said second surface thereby to obtain on said second surface the fingerprints of the next person who grasps said handgrip to operate a door equipped therewith.

2. That improvement defined in claim 1 characterized in that said means providing said first surface is movable relative to said means providing said second surface and is normally positioned to shield said second surface from contact by the fingers of persons normally using said handgrip to open a door equipped with said handgrip.

3. That improvement defined in claim 1 characterized in that said first surface means comprises a cover plate movably supported on said handgrip in a position shielding said second surface means from contact by the fingertips.

4. That improvement defined in claim 1 characterized in that said means for replacing said first surface with said second surface comprises means normally retaining said first and second surfaces in closely spaced side-by-side relation with only said first surface in position to be contacted by the fingers of persons using said handgrip, and said means operable from a control station remote from said handgrip being operable to deactivate said retaining means and for exposing said second surface for contact by the fingertips of the next person using the handgrip.

5. That improvement defined in claim 4 characterized in that said retaining means includes electrically responsive means.

6. That improvement defined in claim 4 characterized in that said retaining means includes electro-magnetic means operable to release said first surface for movement to a position exposing said second surface.

7. A door handgrip having a main body rigidly securable to a door, an outer handgrip member movably mounted thereon and engageable by the fingers of persons to open a door equipped therewith, means normally retaining said handgrip member in a position concealing an underlying handgrip surface, and means operable from a remote control station for releasing said retaining means and permitting said outer handgrip member to move to a position exposing said underlying handgrip surface to obtain the fingerprint of a wrongdoer gripping said underlying surface when using said handgrip to open a door.

8. A door handgrip as defined in claim 7 characterized in that said retaining means comprises electrically responsive means operable to release said outer handgrip member from a control station remote from said handgrip.

9. A door handgrip as defined in claim 7 characterized in that said outer handgrip member is gravity actuated when released to move to a lower level wherein said underlying handgrip surface is exposed.

10. A fingerprint recording accessory installable on a door to obtain the fingerprint of a person endeavoring to use the door while engaged in an illegal act, said accessory comprising cover means mountable on a door in a position providing a normally used fingergrip for opening the door and concealing surface means free of fingerprints, and means controllable from a control station remote from the door for moving said cover means to a position exposing said surface means free of fingerprints thereby to obtain the fingerprints of the next person to use a door equipped with said recording accessory.

11. A recording accessory as defined in claim 10 characterized in the provision of support means for said cover means adapted to be adhesively bonded to a door handgrip to support said cover means normally concealed from view by persons approaching the door to leave a room equipped with the door.

12. A recording accessory as defined in claim 10 characterized in that said cover means includes hinge means having a portion thereof rigidly securable to a door handgrip and effective to support said cover means normally flush against an area of the grip contacted by the fingers of a person attempting to open the door, and said cover means being movable when released to pivot through an arc of 90° or more to a position exposing an area of the handgrip for contact with a user's finger tips.

* * * * *